United States Patent [19]
Harada et al.

[11] Patent Number: 4,769,486
[45] Date of Patent: Sep. 6, 1988

[54] METHOD FOR RACEMIZING AN OPTICALLY ACTIVE AMINO ACID

[75] Inventors: Tsuneo Harada, Shin-nanyo; Kiyotaka Oyama, Hikari, both of Japan

[73] Assignee: Toyo Soda Manufacturing Co., Ltd., Shin-nanyo, Japan

[21] Appl. No.: 89,551

[22] Filed: Aug. 26, 1987

[30] Foreign Application Priority Data

Aug. 26, 1986 [JP] Japan .................. 61-198096

[51] Int. Cl.$^4$ ............................................. C07B 55/00
[52] U.S. Cl. .................................... 562/401; 548/344; 548/496; 548/572; 562/443; 562/444; 562/445; 562/446; 562/554; 562/555; 562/557

[58] Field of Search ............... 562/401, 554, 555, 557, 562/443, 444, 445, 446; 548/344, 496, 572

[56] References Cited

U.S. PATENT DOCUMENTS

| | | | |
|---|---|---|---|
| 2,071,327 | 2/1937 | Bley | 562/401 |
| 3,213,106 | 10/1965 | Sasaji et al. | 562/401 X |
| 4,401,820 | 8/1983 | Chibata et al. | 548/344 |

Primary Examiner—Werren B. Lone
Assistant Examiner—Vera C. Clarke
Attorney, Agent, or Firm—Oblon, Fisher, Spivak, McClelland & Maier

[57] ABSTRACT

A method for racemizing an optically active amino acid, which comprises heating the optically active amino acid in an aqueous solution under an alkaline condition in the presence of an alkali metal salt.

8 Claims, No Drawings

METHOD FOR RACEMIZING AN OPTICALLY ACTIVE AMINO ACID

BACKGROUND OF THE INVENTION

1. Field of the Invention

The present invention relates to a method for racemizing an optically active amino acid.

2. Discussion of the Background

Optically active amino acids are compounds useful as organic industrial chemicals, food additives, feeds and intermediates for agricultural chemicals and medicines.

Optically active amino acids are obtainable usually in the form of racemic modifications by usual syntheses, and useful optical isomers are obtainable by optical resolution. Accordingly, by racemizing the optical antipodes remaining after the optical resolution and repeating the resolution, it is possible to convert them into the useful optical isomers. Here, the racemization is a very important technique.

As a conventional technique, it is known to conduct racemization slowly by heating an optically active amino acid together with a concentrated base or strong acid for a long period of time. In order to conduct the racemization quickly, a high temperature and high pressure are required, whereby a part or whole of the amino acid is likely to decompose depending upon the type of the amino acid.

SUMMARY OF THE INVENTION

It is an object of the present invention to provide a method whereby the racemization reaction under a high temperature and high pressure condition leading to decomposition of an amino acid, is completed in a short period of time to minimize the production of impurities due to the decomposition or polymerization and which is advantageous from the installation or economical point of view.

The present invention provides a method for racemizing an optically active amino acid, which comprises heating the optically active amino acid in an aqueous solution under an alkaline condition in the presence of an alkali metal salt.

The present invention is based on a discovery that when the racemization reaction is conducted in the presence of an alkali metal salt, the reaction rate surprisingly increases, and this effect is remarkable under an alkaline condition, particularly at a pH of at least 10.

DETAILED DESCRIPTION OF THE PREFERRED EMBODIMENTS

The additive to be used for carrying out the racemization includes one or more members selected from the group consisting of salts of alkali metals in Group I of the Periodic Table including lithium, sodium and potassium. The anion may be an inorganic ion such as $Cl^-$, $SO_4^{2-}$ or $NO_3^-$.

The effects of the addition of the alkali metal salt are remarkable under an alkaline condition, and the order of the effects is Li>>Na>K. In particular, by an addition of LiCl, the reaction rate increases by 4.5 times. (See Table 1.)

The concentration of the alkali metal salt is usually at least 0.2M, preferably at least 0.5M, more preferably at least about 1M. There is no particular restriction as to the upper limit, and a high concentration may be employed within the range for the solubility.

There is no particular restriction as to the optically active amino acid. However, a particularly good result has been obtained with phenylalanine.

There is no particular restriction as to the heating temperature. However, the heating temperature is preferably at least 80° C., more preferably at least 100° C. from the installation or economical point of view taking into account e.g. the reaction time. The upper limit is at a temperature above which the amino acid undergoes decomposition, which is usually about 300° C. From the practical point of view, the upper limit is at most 250° C.

The progress of the reaction can be monitored by measuring the specific rotation of the aqueous solution having a predetermined concentration.

TABLE 1

Effects of the addition of a salt under an alkaline condition.

| Added salt | Reaction rate |
| --- | --- |
| None | 1.00 |
| LiCl [2 M] | 4.5 |
| NaCl [2 M] | 1.5 |
| Na$_2$SO$_4$ [1 M] | 1.3 |
| KCl [2 M] | 1.1 |

Now, the present invention will be described in further detail with reference to Examples. However, it should be understood that the present invention is by no means restricted to such specific Examples.

EXAMPLE 1

Into a pressure reactor, 8 ml of an aqueous solution containing 4% by weight of L-phenylalanine and 2M NaCl and having the pH adjusted to 13 by sodium hydroxide, was introduced, and the reaction was conducted in an oil bath of 190° C. The specific rotation of the reaction solution was measured at predetermined intervals, whereby the following results were obtained.

| Reaction time (min) | $[\alpha]_D^{25}$ (C = 1) | Racemization rate (%) |
| --- | --- | --- |
| 0 (Starting material) | −29 | 0 |
| 20 | −24 | 17 |
| 40 | −18 | 38 |
| 60 | −13 | 55 |
| 80 | −10 | 66 |
| 100 | −8 | 73 |
| 120 | −6 | 79 |

EXAMPLE 2

The reaction was conducted in the same manner as in Example 1 except that the reaction solution was prepared to contain 4% by weight of L-phenylalanine and 2M LiCl with a pH of 12.2.

| Reaction time (min) | $[\alpha]_D^{25}$ (C = 1) | Racemization rate (%) |
| --- | --- | --- |
| 0 (Starting material) | −29 | 0 |
| 20 | −15 | 48 |
| 40 | −6.5 | 78 |
| 60 | −3 | 90 |
| 80 | −2 | 93 |
| 100 | −1 | 97 |
| 120 | 0 | 100 |

EXAMPLE 3

The reaction was conducted in the same manner as in Example 1 except that the reaction solution was prepared to contain 4% by weight of L-phenylalanine and 1M $Na_2SO_4$ with a pH of 13.

| Reaction time (min) | $[\alpha]_D^{25}$ (C = 1) | Racemization rate (%) |
|---|---|---|
| 0 (Starting material) | −27 | 0 |
| 20 | −22 | 18.5 |
| 40 | −17 | 37 |
| 60 | −14 | 48 |
| 80 | −11 | 59 |
| 100 | −9 | 67 |
| 120 | −7 | 74 |

EXAMPLE 4

The reaction was conducted in the same manner as in Exmple 1 except that the reaction solution was prepared to contain 4% by weight of L-phenylalanine and 2M KCl with a pH of 13.

| Reaction time (min) | $[\alpha]_D^{25}$ (C = 1) | Racemization rate (%) |
|---|---|---|
| 0 (Starting material) | −29 | 0 |
| 20 | −24 | 17 |
| 40 | −21 | 28 |
| 60 | −17 | 41 |
| 80 | −13 | 55 |
| 100 | −11 | 62 |
| 120 | −10 | 66 |

COMPARATIVE EXAMPLE 1

The reaction was conducted in the same manner as in Example 1 except that the reaction solution was prepared to contain 4% by weight of L-phenylalanine with a pH of 13.

| Reaction time (min) | $[\alpha]_D^{25}$ (C = 1) | Racemization rate (%) |
|---|---|---|
| 0 (Starting material) | −34 | 0 |
| 20 | −28.5 | 16 |
| 40 | −24.5 | 28 |
| 60 | −20.5 | 40 |
| 80 | −17 | 50 |
| 100 | −13 | 62 |
| 120 | −11 | 68 |

COMPARATIVE EXAMPLE 2

The reaction was conducted in the same manner as in Example 1 except that the reaction solution was prepared to contain 1% by weight of L-phenylalanine and 2M NaCl.

| Reaction time (min) | $[\alpha]_D^{25}$ (C = 1) | Racemization rate (%) |
|---|---|---|
| 0 (Starting material) | −32 | 0 |
| 20 | −27 | 16 |
| 40 | −22 | 31 |
| 60 | −17 | 47 |
| 80 | −14 | 56 |
| 100 | −11 | 66 |
| 120 | −9 | 72 |

As described in the foregoing, according to the method of the present invention, the reaction rate is improved, whereby a racemic amino acid can be obtained very advantageously from the viewpoint of the operation, installation and economy.

What is claimed is:

1. A method for racemizing an optically active amino acid, which comprises heating the optically active amino acid in an aqueous solution under an alkaline condition in the presence of in a concentration of at least 1.2M of an alkali metal salt.

2. The method according to claim 1, wherein the optically active amino acid is phenylalanine.

3. The method according to claim 1, wherein the alkaline condition is a pH of at least 10.

4. The method according to claim 1, wherein the alkali metal salt is one or more members selected from the group consisting of inorganic salts of lithium, sodium and potassium.

5. The method according to claim 1, wherein the temperature for the heating is at least 100° C.

6. The method according to claim 5, wherein the temperature for the heating is at most 250° C.

7. The method according to claim 1, wherein the alkali metal salt is lithium chloride.

8. The method according to claim 4, wherein the anion of the inorganic salts is $Cl^-$, $SO_4^{2-}$ or $NO_3^-$.

* * * * *